United States Patent [19]

Andrews

[11] Patent Number: 4,591,341
[45] Date of Patent: May 27, 1986

[54] ORTHODONTIC POSITIONER AND METHOD OF MANUFACTURING SAME

[76] Inventor: Lawrence F. Andrews, 2025 Chatsworth Blvd., San Diego, Calif. 92107

[21] Appl. No.: 657,308

[22] Filed: Oct. 3, 1984

[51] Int. Cl.⁴ .............................................. A61C 3/00
[52] U.S. Cl. ........................................ 433/6; 433/187
[58] Field of Search ......................... 433/6, 184, 187; 128/136

[56] References Cited

U.S. PATENT DOCUMENTS

| 310,233 | 1/1885 | Spyer et al. | 433/184 |
|---|---|---|---|
| 1,463,968 | 8/1923 | Petry | 433/187 |
| 1,537,716 | 5/1925 | Twiggs | 433/184 |
| 3,178,820 | 4/1965 | Kesling | 433/6 |
| 3,496,936 | 2/1970 | Gores | 433/6 |
| 3,510,946 | 5/1970 | Kesling | 433/6 |
| 3,950,851 | 4/1976 | Bergersen | 433/6 |
| 4,055,895 | 11/1977 | Huge | 433/6 |

OTHER PUBLICATIONS

Jermyn, Multiple Suction Cup Dentures, Oct. 1967, Journal of Prosethic Dentistry, pp. 316-325.

Primary Examiner—John J. Wilson
Attorney, Agent, or Firm—Townsend and Townsend

[57] ABSTRACT

An improved orthodontic positioner provides a series of tiny suction devices on the tooth confronting walls of the positioner. These suction devices provide increased adherence of the positioner to the top, inner and outer tooth surfaces of the patient's teeth, and act to mechanically hold the teeth firmly together in their desired place within the positioner.

5 Claims, 3 Drawing Figures

U.S. Patent May 27, 1986 4,591,341
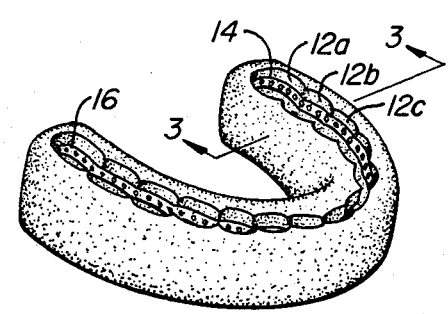
FIG._1.
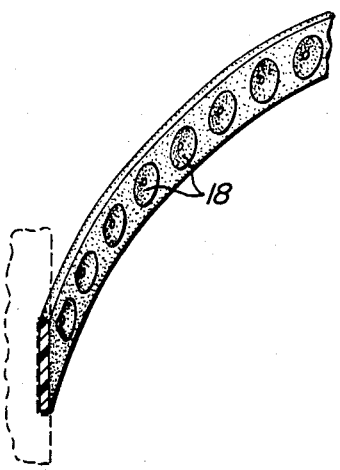
FIG._2.
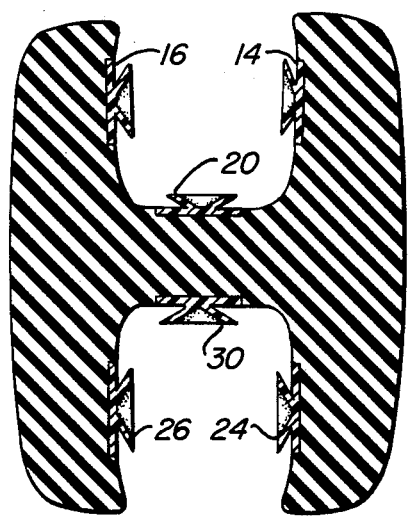
FIG._3.

ORTHODONTIC POSITIONER AND METHOD OF MANUFACTURING SAME

BACKGROUND OF THE INVENTION

1. Field of the Invention.

This invention relates generally to dental equipment and practices, and specifically to an improved orthodontic positioner for improving the position of a patient's teeth, and a method for its manufacture.

2. Description of the Prior Art

In standard orthodontic practice, sometimes several steps are utilized to achieve the desired degree of straightening and positioning of the teeth. Typically, orthodontic braces utilizing first a system of bands, brackets, and wires, that are installed on the teeth, are left in place for a period of time to mechanically orient the imperfect occlusion. However, when bands are used they occupy significant space in and around the teeth, making it impossible to fully complete treatment until they are removed. Precise vertical positioning of the teeth is also difficult to achieve fully with braces. Final correction requires some slight further tooth movement to complete space closure and vertical positioning. This is usually accomplished through the use of an orthodontic positioner, which is an elastic structure much in the form of a boxer's mouthpiece.

The positioner is made by first constructing plaster reproductions of the patient's actual teeth at the end of the braces portion of treatment. These reproductions are placed into the ideal alignment desired for the patient's actual teeth. Pliable rubber or silicone plastic is then molded around these ideally positioned teeth, then cured to a permanent but still elastic form. The resulting set of impressions in the cured positioner material thus correspond to the desired ultimate positioning of the patient's teeth. The completed positioner is then inserted into the mouth by the patient and, by clenching the teeth, are contacted by the molded impressions in the positioner and are thus urged into their ideal positions.

Such conventional orthodontic positioners are well known. However, most of these devices are hindered in their operation by an inherent biological fact of life-that is, for most of the time, a patient's jaws are relaxed. Thus, when the orthodontic positioner is in place in the user's mouth, the patient must actively keep his teeth clenching for the positioner to work. Jaw physiology, human nature and fatigue being what they are, the user is prone to let his jaws relax, allowing the teeth to leave their ideal locations within the positioner, thus reducing the efficiency of the entire system. Therefore, the rate of tooth movement is slower than optimum which increases the length of time that the positioner must be worn to achieve ideal tooth alignment.

SUMMARY OF THE INVENTION

The present invention provides an improved orthodontic positioner which assists in keeping the patient's teeth together through the use of a series of tiny suction devices on the tooth confronting walls of the positioner. These suction devices provide increased adherence of the positioner to the top, inner, outer, and around the rear surface of the last tooth of the patient's dentition, thus mechanically holding the teeth firmly together in their desired place within the positioner. This improved retention of the patient's teeth within the positioner accelerates the desired tooth movement and correction because the force is more continuous.

Furthermore, the incorporation of these suction devices on the tooth confronting walls of the positioner serves to add a second level of flexibility to the positioner, in addition to the level of flexibility achieved by the natural flexibility of the substance used to make the positioner itself. It is believed that this additional flexibility enhances the gentle urging of the teeth to their desired positions, thus accelerating the rate of movement and reducing the amount of time the positioner must be worn.

In the preferred embodiment, the suction devices are formed of tiny elastic suction cups (e.g., rubber, silicone, etc.), each no wider than the tooth surface it must confront, and ideally much smaller. In fact, it is desirable to have a plurality of suction cups placed in the positioner to confront the top, inner and outer surfaces of each tooth in question. These suction cups present small, hemispherically-shaped flexible surfaces to the teeth they confront, and, when pressed into place by biting, provide a gentle but significant suction to grab and direct the teeth to their desired position with the body of the positioner providing the outer constraints of control.

The improved orthodontic positioner of this invention is preferably made in the following manner: first, as in the construction of a conventional orthodontic positioner, plaster reproductions of the patient's actual teeth are made. The teeth of these plaster reproductions are then arranged so that they represent the ideal alignment desired for the patient's actual teeth. A plurality of suction devices, preferably in the form of "strips" of tiny suction cups, are then placed on the top, inner and outer surfaces of these plaster teeth, so that each tooth's surface is contacted by at least one, and preferably a plurality, of suction devices. A flexible, formable material, such as rubber, silicone, plastic or the like, is then formed around the plaster reproductions with the suction devices intact. The semi-liquid material is cured and allowed to solidify. The plaster cast is then removed from the newly cured positioner. In this way, the suction devices are integrally incorporated into the walls of the orthodontic positioner, yielding a perfect, custom tailered pattern to which the patient's actual teeth can conform.

BRIEF DESCRIPTION OF THE DRAWINGS

FIG. 1 is a perspective view of the improved orthodontic positioner of this invention;

FIG. 2 is a perspective view of a strip of suction devices; and

FIG. 3 is a cross-sectional view taken along line 3—3 of FIG. 1.

DETAILED DESCRIPTION OF THE PREFERRED EMBODIMENT

FIG. 1 is a perspective view of an orthodontic positioner 10, with molded depressions 12a, b, etc., corresponding to the individual teeth in the arrangement from which the positioner was cast. The first strip of suction devices 14 is shown on the wall of positioner 10 which will confront the outer surface of that row of teeth. A second strip of suction devices 16 is shown on the wall of positioner 10 which will confront the inner surface of that row of teeth. Further strips of such suction devices are located on the wall of positioner 10 which will confront the top (or chewing) surface of the teeth but these cannot be seen in the view of FIG. 1.

FIG. 2 is a view of a strip of suction devices, showing the individual suction cups 18 mounted in strip form. Of course, there can be any number of suction cups 18 located on the strip.

FIG. 3 is a cross-sectional view taken along line 3—3 of FIG. 1. In this view, outer strip 14 and inner strip 16 can be seen on their respective walls while top or chewing surface strip 20 can now be seen as it would confront that surface of the teeth. There can be, of course, a corresponding set of depressions and strips of suction devices on the positioner of the lower set of the patient's teeth. This is indicated in FIG. 3 by lower outer strip 24, lower inner strip 26 and lower chewing strip 30.

What is claimed as invention is:

1. An orthodontic positioner for urging at least one of a dental patient's teeth from an actual position to a desired position, the orthodontic positioner comprising:
    a flexible mouthpiece formed to have therein impressions of the desired positions of the teeth; and
    a tooth-adhering portion comprising a suction device interior of at least one of the impressions for grasping a selected tooth and urging the selected tooth from the actual position to the desired position with suction forces.

2. An orthodontic positioner comprising:
    a flexible mouthpiece into which impressions of the desired alignments of a dental patient's teeth have been made, at least one of said desired alignment being different from an actual alignment of at least one selected tooth, to be worn by the patient to urge the at least one selected tooth into such desired alignment by applying gentle pressure to the at least one selected tooth along tooth-confronting surfaces of said positioner; and
    a tooth adhering portion comprising a suction device interior of at least one of the impressions to increase the adherence of said positioner to at least one of said teeth, and more securely maintain said teeth within said positioner, the suction device being positioned to confront a surface of the at least one selected tooth and thereby urge the at least one selected tooth toward said desired alignment.

3. The orthodontic positioner of claim 1 wherein said suction device comprises a suction cup member presenting a flexible hemispherically-shaped surface to said teeth.

4. The orthodontic positioner of claim 1 wherein said positioner includes surfaces for confronting the top, inner and outer surfaces of said teeth and said tooth adhering portion comprises strips of suction cups carried on each of said tooth confronting surfaces.

5. A method manufacturing an orthodontic positioner comprising the steps of:
    providing solid reproductions of a patient's teeth;
    arranging said reproductions in a mold so they represent the ideal alignment of said patient's teeth;
    placing a plurality of suction devices on the top, inner and outer surfaces of said reproductions;
    pouring a flexible material around these plaster reproductions with said suction devices intact;
    allowing said flexible material to solidify; and
    removing the resulting cast from the reproduction mold.

* * * * *